United States Patent [19]

Rollick

[11] Patent Number: 4,719,305
[45] Date of Patent: Jan. 12, 1988

[54] PROCESS FOR THE PREPARATION OF N,N-DIISOPROPYLBENZOTHIAZYL-2-SULFENAMIDE

[75] Inventor: Kevin L. Rollick, Munroe Falls, Ohio

[73] Assignee: The Goodyear Tire & Rubber Company, Akron, Ohio

[21] Appl. No.: 713,066

[22] Filed: Mar. 18, 1985

[51] Int. Cl.$^4$ .......................................... C07D 277/80
[52] U.S. Cl. .................................................... 548/168
[58] Field of Search ................................ 548/167, 168

[56] References Cited

U.S. PATENT DOCUMENTS

| | | | |
|---|---|---|---|
| 2,417,989 | 3/1947 | Moore et al. | 548/167 |
| 2,419,283 | 4/1947 | Paul et al. | 548/189 |
| 2,762,814 | 9/1956 | Lunt | 548/167 |
| 2,776,297 | 1/1957 | Cherlow | 548/168 |
| 2,807,621 | 9/1957 | Cooper et al. | 548/167 |
| 2,885,405 | 5/1959 | D'Amico | 548/167 |
| 2,992,228 | 7/1961 | D'Amico | 548/167 |

FOREIGN PATENT DOCUMENTS 897708  3/1984  Belgium .

OTHER PUBLICATIONS

English Translation of Belgium Pat. No. 897,708.

*Primary Examiner*—Mary E. Ceperley
*Attorney, Agent, or Firm*—M. R. Dion, Sr.

[57] ABSTRACT

There is disclosed a process for the preparation of N,N-diisopropylbenzothiazyl-2-sulfenamide which comprises contacting an aqueous mixture of diisopropylamine and 2-mercaptobenzothiazole with an oxidizing agent in the presence of sufficient acid to neutralize the excess base, if any, in the oxidizing agent wherein the molar ratio of diisopropylamine to 2-mercaptobenzothiazole is at least 1.5 to 1.

8 Claims, No Drawings

PROCESS FOR THE PREPARATION OF N,N-DIISOPROPYLBENZOTHIAZYL-2-SULFENAMIDE

FIELD OF THE INVENTION

This invention relates to sulfenamides. More particularly, it relates to benzothiazyl-2-sulfenamides, especially N,N-diisopropylbenzothiazyl-2-sulfenamide. Still more particularly, it relates to a new process for preparing N,N-diisopropylbenzothiazyl-2-sulfenamide.

BACKGROUND ART

Since the advent of 2-mercaptobenzothiazole as a rubber vulcanization accelerator, extensive investigation has been conducted to uncover derivatives thereof useful for the same purpose. Among such derivatives which have been found of particular value are various benzothiazyl sulfenamides. In particular, N,N-diisopropylbenzothiazyl-2-sulfenamide has been found to be a particularly outstanding delayed action accelerator for both natural and synthetic rubbers.

Various procedures have been proposed for preparing benzothiazyl-2-sulfenamides in general. For instance, U.S. Pat. No. 2,417,989 teaches the process of producing a sulfenamide by adding an aqueous solution of an oxidizing agent and an aqueous solution of an aryl thiazole, in the form of a water soluble alkali metal mercaptide, separately and concurrently to an aqueous solution of an amine or an amine salt. U.S. Pat. No. 2,419,283 teaches a process for the preparation of sulfenamides wherein an alkali metal sulfate, for example, sodium sulfate is present during the oxidation reaction between an oxidizing agent, a mercaptan and an amine. U.S. Pat. No. 2,776,297 teaches a process for preparing N,N-diisopropylbenzothiazyl-2-sulfenamide by reacting a metallic or ammonium salt of mercaptobenzothiazole with N-chlorodiisopropylamine in an aqueous medium, conducted in the presence of at least a minimum amount of diisopropylamine and under controlled conditions of hydrogen ion concentration. Belgian Pat. No. 897,708 discloses a process for preparing benzothiazyl-2-sulfenamides by reacting sodium mercaptobenzothiazole with an amine in an alcohol/water solution.

Nowhere in the prior art has it been disclosed that N,N-diisopropylbenzothiazyl-2-sulfenamide can be prepared by contacting an aqueous mixture of diisopropylamine and 2-mercaptobenzothiazole with an oxidizing agent in the presence of sufficient acid to neutralize the excess base, if any, in the oxidizing agent.

DISCLOSURE OF THE INVENTION

In accordance with the practice of the present invention there is disclosed a process for the preparation of N,N-diisopropylbenzothiazyl-2-sulfenamide which comprises contacting an aqueous mixture of diisopropylamine and 2-mercaptobenzothiazole with an oxidizing agent in the presence of sufficient acid to neutralize the excess base, if any, in the oxidizing agent wherein the molar ratio of diisopropylamine to 2-mercaptobenzothiazole is at least 1.5 to 1.

One of the unusual aspects of the process of this invention is the fact that neither preformed N-chlordiisopropylamine nor the water soluble salt of mercaptobenzothiazole need be employed as reactants, thereby eliminating the processing steps needed to produce them and the equipment required to store them.

The process of the present invention can be carried out either continuously or on a batchwise basis. In a typical continuous process, a premix containing the diisopropylamine and 2-mercaptobenzothiazole (MBT) in a molar ratio of 1.5 to 1 amine to MBT, admixed with a sufficient quantity of water to make a pumpable slurry, is continously fed to a stirred tank reactor and contacted with 1.1 to 1.5 molar equivalents of oxidizing agent based on the MBT and sufficient acid to neutralize the excess base, if any, in the oxidizing agent. The reaction temperature is maintained in a range of from 35° C. to 65° C. for a residence time of between 5 and 30 minutes. While there is no definite upper limit on the molar ratio of the amine to the MBT used in the premix, the upper limit is only constrained by economics and by the difficulty of product recovery at the higher molar ratios. While higher reaction residence times may be used, they would be of no special advantage. The process can be carried out at atmospheric pressure or under positive pressure. The presence of a vacuum would only serve to remove the amine from the reaction mixture. The process may be carried out in air or any suitable inert atmosphere. The reactor effluent contains spent oxidizing agent, unreacted amine and the product which may be recovered by any conventional means.

The types of oxidizing agents suitable for use in the process of this invention are the alkali metal and alkaline earth metal hypohalites. These generally contain excess base to stabilize the oxidizing agent in the solutions. Typical of the hypohalites are: sodium hypochlorite, potassium hypochlorite, calcium hypochlorite, magnesium hypochlorite, sodium hypobromite, potassium hypobromite, calcium hypobromite, etc. The level of the oxidizing agent used is 1.1 to 1.5, preferably 1.15 to 1.3 molar equivalents of oxidizing agent per mole of 2-mercaptobenzothiazole. While the upper limits of oxidizing agents have been specified at 1.5 molar equivalents, higher levels may be used. However, it is believed that higher levels of oxidizing agent can have a detrimental effect on the finished product produced. Any acid may be used in the practice of the process of this invention which will neutralize the excess base, if any, of the oxidizing agent solution. Typical acids are sulfuric, phosphoric, hydrochloric, and acetic. As is disclosed in the examples herein, a slightly basic material such as sodium bicarbonate can also be used to perform the acidic function of neutralizing the excess base of the oxidizing agent.

In a typical batch process for carrying out this invention, a mixture of the amine, the 2-mercaptobenzothiazole and the acid are added to a reactor with a sufficient quantity of water to make the mixture stirrable. The temperature is controlled at 35° C. to 65° C., preferably 50° C. to 60° C. The oxidizing agent is then added to the reaction mixture over 10 to 30 minutes or at such a rate so as to maintain temperature control. After the oxidizing agent has been added, the mixture is agitated for an additional period of time to allow completeness of reaction. At the end of that additional reaction period the product may be separated from the mixture by any conventional means. For example, the product being in the organic layer may be decanted from the aqueous layer followed by flash distillation under reduced pressures to remove the excess amine or the entire reaction mixture may be quenched with a large quantity of cold water to precipitate the product from the mixture.

The following examples serve to illustrate not to limit the process of this invention.

EXAMPLE I 17 mL of an aqueous solution of the sodium salt of 2-mercaptobenzothiazole (2.91 molar, 0.05 moles) and 28 mL of diisopropylamine (0.20 moles) were combined in a 250 mL 3-neck flask. Keeping the temperature below 40° C., 8 mL of 25% sulfuric acid was added (0.07 moles). This amount of acid was sufficient to convert the sodium salt of 2-mercaptobenzothiazole to mercaptobenzothiazole and to neutralize the excess base anticipated from the oxidizing agent. Next, 26 mL of sodium hypochlorite solution (2.36 molar, 0.06 moles) was added dropwise over one hour allowing the temperature to reach 50° C. The reaction was stirred for an additional hour at 50° C. then cooled in an ice bath and diluted to 250 mL with cold water. The white precipitate was collected in a Buchner funnel, washed with cold water and dryed. A yield of 10.4 g. (78%) of N,N-diisopropyl-2-benzothiazyl-sulfenamide melting at 58° to 59° C. was obtained.

EXAMPLE II 25 mL of diisopropylamine (0.179 moles) was combined in a 250 mL 3-neck flask with one mL of water and 0.75 mL acetic acid (0.012 moles). To this solution was added 4.18 g. (0.025 moles) of 2-mercaptobenzothiazole. Then 13 mL (0.03 moles) of sodium hypochlorite solution was added over 30 minutes allowing the temperature to rise to 35° C. The reaction was then heated to 50° C. for one hour, then cooled to 0° C. and diluted to 200 mL with cold water. The product was collected in a Buchner funnel, washed with cold water and dryed. A yield of 5.7 g. (86%) of N,N-diisopropyl-2-benzothiazyl-sulfenamide material melting at 56° to 58° C. was obtained.

EXAMPLE III

The reaction described in Example II was rerun using 0.5 mL (0.007 moles) of phosphoric acid in place of acetic acid. A yield of 5.5 g. (83%) of N,N-diisopropyl-2-benzothiazyl-sulfenamide material melting at 55° to 58° C. was obtained.

EXAMPLE IV

The reaction described in Example II was rerun using 1.1 g. (0.0125 moles) of sodium bicarbonate in place of acetic acid. A yield of 5.6 g. (84%) of N,N-diisopropyl-2-benzothiazyl-sulfenamide material melting at 56.5° to 58.5° C. was obtained.

EXAMPLE V

N-chlorodiisopropylamine was prepared by dropwise addition of 50.5 g. (0.5 moles) diisopropylamine to 230 mL (2.63 molar, 0.6 moles) sodium hypochlorite solution keeping the temperature below 10° C. The reaction was stirred at 0° C. for two hours after addition was complete. It was then transferred to a separatory funnel and the aqueous layer drawn off. The product, N-chlorodiisopropylamine, was washed with 50 mL of saturated sodium chloride salt solution, dryed with sodium sulfate, and drained into a tared flask. A yield of 67.1 grams (99%) of N-chlorodiisopropylamine, 99.8% pure was realized.

To a 250 mL 3-neck flask containing 20 mL diisopropylamine (0.14 moles) and 1 mL water was added 4.18 g. (0.025 moles) 2-mercaptobenzothiazole. After thorough mixing of the suspension, N-chlorodiisopropylamine (4.1 g., 0.03 moles) was added dropwise over 20 minutes allowing the temperature to rise to 40° C. The reaction was stirred at room temperature for one hour then heated to 55° C. for one hour. Addition of 50 mL water dissolved the salts formed during the reaction. The mixture was then cooled in an ice bath to precipitate the produce. Addition of additional water and ice to a volume of 200 mL completed the precipitation of the product which was filtered, washed and dryed. A yield of 5.5 g. (83%) of N,N-diisopropylbenzothiazyl-2-sulfenamide material melting from 56.5° to 58° C. was obtained.

EXAMPLE VI

To a 500 mL 3-neck flask, equipped with agitation was added 37.4 g. of 2-mercaptobenzothiazole (0.224 moles), 150 mL water and 45.2 g. diisopropylamine (0.448 moles) resulting in a temperature rise to 40° C. After cooling the mixture to 37° C., 80.0 g. sodium sulfate (0.56 moles) was added. While controlling the temperature at 33° C. to 37° C., 162 mL of a 10% aqueous solution of sodium hypochlorite (0.25 moles) was added at 32 mL/h. At the end of the sodium hypochlorite addition, the mixture was turbid, therefore an additional 0.5 h. of agitation was provided with no apparent change. The product was extracted with ether, leaving behind a considerable amount of insoluble material. The ether extracts were dried with anhydrous sodium sulfate, filtered and the ether removed by vacuum. Yielded 34 g. (57%) of N,N-diisopropylbenzothiazyl-2-sulfenamide material melting at 54° to 57° C.

EXAMPLE VII

The experiment of Example VI was repeated with the reaction at 55° C. No significant differences were noted. Yielded 33.1 g. (56%) of N,N-diisopropylbenzothiazyl-2-sulfenamide, material melting at 55°–58° C.

EXAMPLE VIII

In a high agitation reactor, 8.36 g. of 2-mercaptobenzothiazole (0.05 moles) was added to 8.0 g. water and stirred slowly to wet the MBT. With the reactor in a water bath at 55° C., 10.1 g. diisopropylamine (0.1 moles) was added and the mixture stirred until smooth. Next, 0.5 g. aqueous sulfuric acid (0.005 moles), diluted in 2 g. water, was added followed by dropwise addition of 39 mL of sodium hypochlorite solution (1.8 molar; 0.07 moles) containing 10.4 g/L free sodium hydroxide. The reaction was completed, as evidenced by the disappearance of solids in the mixture, about 10 minutes after addition of the oxidizing agent. The product was recovered by quenching in 100 mL water, filtering and drying. Yield of 10.7 g. (80%) of N,N-diisopropylbenzothiazyl-2-sulfenamide, material melting at 55°–57° C.

EXAMPLE IX

The experiment of Example VIII was repeated except that the molar ratio of amine to MBT was 1.5:1 rather than 2:1. To complete the reaction, the amount of oxidizing agent required was 40 mL. Yield of 10.6 g. (80%) of N,N-diisopropylbenzothiazyl-2-sulfenamide, material melting at 54°–57° C.

EXAMPLE X

Example VIII was repeated with the further addition of 17.1 g. sodium sulfate (0.12 moles) prior to the oxidizing agent and the reaction mixture was stirred an additional 1.5 h to yield a semi-solid product layer on top of the mixture and salt crystals on the bottom. The product was precipitated by pouring the mixture into 200 mL of water, stirring to dissolve the salts, filtering and drying. Yield of 10.1 g. (76%) of N,N-diisopropylbenzothiazyl-2-sulfenamide, material melting at 56°–59° C.

EXAMPLE XI

Example X was repeated but the sulfuric acid was deleted and the sodium sulfate was increased to 17.9 g. (0.126 moles). The reaction was incomplete after 2 h additional reaction time following the oxidizing agent addition. The product was recovered as above. Yield of 8.25 g. (62%) presumably of a mixture of N,N-diisopropylbenzothiazyl-2-sulfenamide and unreacted 2-mercaptobenzothiazole material melting at 57°–158° C.

As can be seen, the process of the present invention, as illustrated by Examples I through IV, VIII and IX when compared to the prior art processes as shown in Examples V through VII, X and XI show that N,N-diisopropylbenzothiazyl-2-sulfenamide can be prepared without the need for employing N-chlorodiisopropylamine, salt or other catalysts.

While certain representative embodiments and details have been shown for the purpose of illustrating the invention, it will be apparent to those skilled in this art that various changes and modifications may be made therein without departing from the scope of the invention.

What is claimed is:

1. A process for the preparation of N,N-diisopropylbenzothiazyl-2-sulfenamide consisting of:

(a) forming a premix of diisopropylamine and 2-mercaptobenzothiazole (MBT) in a molar ratio of at least 1.5:1, amine:MBT, in sufficient water to form a pumpable slurry;
   (b) adding to the premix 1.1 to 1.5 molar equivalents based on the MBT of a aqueous oxidizing agent solution selected from the group of solutions consisting of alkali metal hypohalites and alkaline earth metal hypohalites containing a stabilizing amount of a base, in the presence of a sufficient quantity of an acid to neutralize the base contained in the oxidizing agent solution;
   (c) controlling the temperature during the oxidizing agent solution addition from 35° C. to 65° C.; and
   (d) recovering the product.

2. The process according to claim 1 wherein the oxidizing agent is sodium hypochlorite.

3. The process according to claim 1 wherein the oxidizing agent is potassium hypochlorite.

4. The process according to claim 1 wherein the oxidizing agent is calcium hypochlorite.

5. The process according to claim 1 wherein the oxidizing agent is magnesium hypochlorite.

6. The process according to claim 1 wherein the oxidizing agent is present at a level of 1.15 to 1.3 molar equivalents per mole of mercaptobenzothiazole.

7. The process according to claim 1 wherein the acid is added in the premix step.

8. The process according to claim 1 wherein the acid is added simultaneously with the oxidizing agent solution.

* * * * *